US00PP37092P2

(12) United States Plant Patent
Durio

(10) Patent No.: US PP37,092 P2
(45) Date of Patent: Nov. 11, 2025

(54) ***ILEX* PLANT NAMED 'ROX'**

(50) Latin Name: *Ilex hybrida*
Varietal Denomination: ROX

(71) Applicant: Albert Durio, Opelousas, LA (US)

(72) Inventor: Albert Durio, Opelousas, LA (US)

( * ) Notice: Subject to any disclaimer, the term of this patent is extended or adjusted under 35 U.S.C. 154(b) by 0 days.

(21) Appl. No.: 18/668,286

(22) Filed: May 20, 2024

(51) Int. Cl.
*A01H 5/00* (2018.01)
*A01H 6/00* (2018.01)

(52) U.S. Cl.
USPC ..... Plt./247
CPC ..... *A01H 6/00* (2018.05)

(58) Field of Classification Search
USPC ..... Plt./247
CPC ..... A01H 5/00
See application file for complete search history.

*Primary Examiner* — Kent L Bell

(57) ABSTRACT

A new and distinct cultivar of *Ilex* plant named 'ROX' is disclosed, characterized by a dense canopy of dark green foliage, and abundant red berries. Plants have shown resistance to *Anthracnose*. Without trimming plants can form a full, pyramidal shaped shrub, or grow into a single clear trunk tree by removing lower branches. Plants do not require pruning to maintain a controlled and attractive shape. The new cultivar is an *Ilex*, suitable for ornamental garden purposes.

1 Drawing Sheet

Latin name of the genus and species: *Ilex hybrida.*
Variety denomination: 'ROX'.

BACKGROUND OF THE INVENTION

The new cultivar resulted from a naturally occurring branch mutation of *Ilex* 'Nellie R. Stevens', unpatented. The new variety was discovered in a private garden in Opelousas, Louisiana in April 2016.

After identifying the new variety as a potentially interesting selection, first asexual propagation of 'ROX' occurred by vegetative cuttings at a commercial nursery in New Iberia, Louisiana in October 2016. The inventor continued controlled testing and asexual propagation, assessing stability of the unique characteristics of this variety. Several generations have been reproduced and have shown that the unique features of this cultivar are stable and reproduced true to type.

SUMMARY OF THE INVENTION

The cultivar 'ROX' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ROX' These characteristics in combination distinguish 'ROX' as a new and distinct *Ilex* cultivar:

1. Resistant to Anthracnose.
2. Internodal spacing less than ½ inch.
3. No trimming needed to achieve full/dense plants.
4. Can form a full, pyramidal shaped plant without trimming or single clear trunk trees by removing lower branches.

PARENTAL COMPARISON

'ROX' is similar to the parent variety in most horticultural characteristics, however, plants of 'ROX' differ in the following ways:

1. Plants of the new variety are produced faster than plants of the parent.
2. Internode length of the new variety is shorter than the internode length of the parent.
3. The new variety is resistant to Anthracnose, while the parent variety is not.
4. Plants of the new variety do not require pruning or growth regulators, unlike plants of the parent.
5. Leaf bud sprouts of the new variety result in a denser canopy (no woody bare spots) than leaf bud sprouts of the parent.

COMMERCIAL COMPARISON

'ROX' can be compared to the commercial variety *Ilex* 'Dahoon Holly', unpatented. The varieties are similar in most horticultural characteristics, however, plants of 'ROX' differ in the following ways:

1. Plants of the new variety do not require pruning, while this comparator requires pruning 4 to 5 times per year.
2. Foliage color of the new variety is darker green than the foliage color of this comparator.
3. Plants of the new variety have a denser canopy than plants of this comparator.
4. Berries of the new variety are larger than berries of this comparator.

BRIEF DESCRIPTION OF THE PHOTOGRAPH

The accompanying photograph illustrates in full color a 4 year old plant of the new variety in a 15-gallon pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ROX' plants grown outdoors in Loxley, Alabama. Plants are approximately 2.5 years old, in a 2-gallon nursery container. Measurements and numerical values represent averages of typical plant types.

Botanical classification: *Ilex hybrida* 'ROX'.

PROPAGATION

Typical method: Softwood cuttings in spring and summer.

Root description: Very dense fibrous roots. Colored near RHS Grey-Brown 199C.

PLANT

Growth habit: Upright evergreen shrub. Pyramidal.

Height: Approximately 70 cm.

Plant spread: Approximately 36 cm.

Branching characteristics: Well branched, approximately 4 to 7 primary branches from the center of the plant. Branches occur at approximately 15° to 75° angles. Each primary branch has 3 to 4 lateral branches.

Primary branches:

Length of primary branches: Average range 22 to 38 cm.

Diameter of primary branches: Average range 6 to 12 mm.

Primary branch strength: Very strong, difficult to break.

Primary branch color:

*Oldest wood*.—Near RHS Yellow-Green 146A with streaky scales of Grey-Brown 199A and 199B.

*Immature branches*.—Near RHS Yellow-Green 144A.

Primary branch texture: Glabrous. Oldest wood somewhat rough.

Lateral branches:

Length of lateral branches: Average range 8 to 20 cm.

Diameter of lateral branches: Average 5 mm.

Lateral branch strength: Strong.

Lateral branch color: Near RHS Green 143C.

Lateral branch texture: Glabrous, smooth.

Internode length: Average 8 to 10 mm.

Age of plant described: Approximately 2.5 years.

FOLIAGE

Leaf:

*Type*.—Simple.

*Arrangement*.—Alternate.

*Average length*.—Approximately 3.6 to 7.2 cm.

*Average width*.—Approximately 2 cm to 3 cm.

*Shape of blade*.—Ovate.

*Apex*.—Acute with a sharp serration.

*Base*.—Attenuate, coming nearly obtuse with age.

*Attachment*.—Stalked.

*Margin*.—Entire, or 2 to 4 sharp serrations. Serrations 2 to 4 mm long.

*Texture of top surface*.—Glabrous.

*Texture of bottom surface*.—Glabrous.

*Appearance of top surface*.—Glossy.

*Appearance of bottom surface*.—Matte.

*Color*.—Young foliage upper side: Near RHS Green 143A. Young foliage under side: Near RHS Green 143C. Mature foliage upper side: Near RHS Green 139A. Mature foliage under side: Near RHS Green 137C.

*Venation*.—Type: Pinnate. Venation color upper side: Near RHS Yellow-Green N144B. Venation color under side: Near RHS Yellow-Green N144C.

*Petiole*.—Length: About 7 mm. Diameter: About 3 mm. Color: Upper Surface: Near RHS Yellow-Green 145A. Lower Surface: Near RHS Yellow-Green 1445A.

*Texture*.—Glabrous, upper and lower surfaces.

FLOWER

Female, axillary flowers. Flowering begins around late April in Southern California.

Flower size:

*Diameter*.—10 mm.

*Depth*.—5 mm.

Peduncle:

*Length*.—7 mm.

*Diameter*.—1.5 mm.

*Color*.—Near RHS Green 143C.

*Texture*.—Glabrous.

Petals:

*Arrangement*.—Cruciform.

*Length*.—5 mm.

*Width*.—4 mm.

*Shape*.—Orbicular.

*Margin*.—Entire.

*Apex*.—Rounded.

*Base*.—Broad cuneate.

*Quantity*.—4.

*Texture*.—Glabrous all surfaces.

*Appearance*.—Matte all surfaces.

*Color*.—When opening: Upper surface: Near RHS White 155A. Lower surface: Near RHS White 155A. Fully opened: Upper surface: Near RHS White 155C. Lower surface: Near RHS White 155C.

Bud:

*Shape*.—Globular.

*Length*.—Approximately 5 mm.

*Diameter*.—Approximately 5 mm.

*Color*.—Near RHS Green 143C.

Sepals:

*Quantity*.—4.

*Length*.—1.5 mm.

*Width*.—1 mm.

*Shape*.—Deltate.

*Color*.—Interior Surface: Near RHS Greyed-Purple 183B. Exterior Surface: Near RHS Greyed-Purple 183C.

*Texture*.—All surfaces glabrous.

Fragrance: None detected.

REPRODUCTIVE ORGANS

Stamens:

*Quantity*.—4.

*Filament length*.—Average 2 mm.

*Filament color*.—RHS Greyed-Orange 165D.

Anthers: None.

Pistil:

*Number*.—1, all parts fused into a single globular structure 5 mm long and 4 mm wide. Colored near RHS Yellow-Green 144C.

OTHER CHARACTERISTICS

Disease and pest resistance: Observed resistant to *Anthracnose*. Neither resistance nor susceptibility to other normal diseases and pests of *Ilex* observed. Potential insect problems include holly leaf miner, spider mites, whitefly and scale. Potential disease problems include leaf spot, leaf rot, tar spot and powdery mildew.

Temperature tolerance: USDA Zone 6 through 9.

Fruit/seed production: Berry. Globose, glabrous, about 7 to 8 mm by 7 to 8 mm. colored near RHS Red 45B.

Seed: About 1 to 6 per berry, approximately 1 mm by 1 mm, colored about 203B.

What is claimed is:

1. A new and distinct cultivar of *Ilex* plant named 'ROX' as herein illustrated and described.

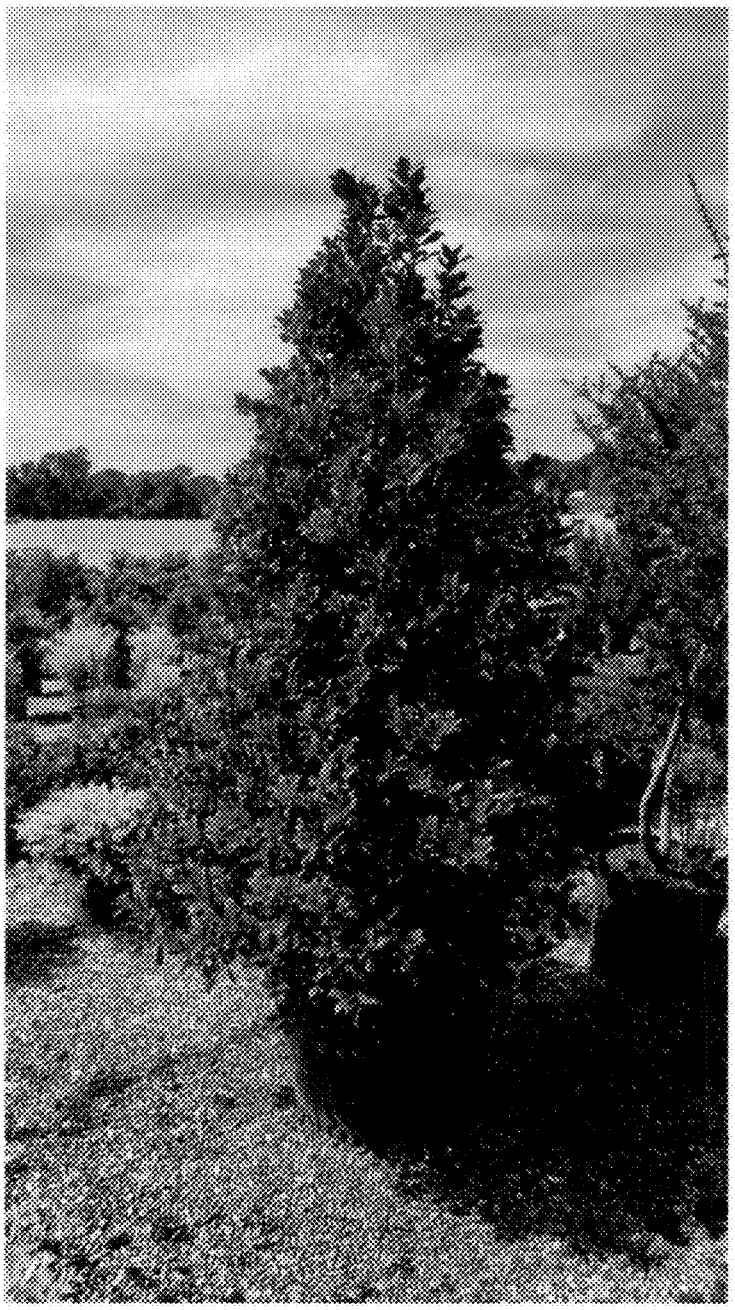

* * * * *